US00PP13690P29

(12) United States Plant Patent
Michalik

(10) Patent No.: US PP13,690 P2
(45) Date of Patent: Apr. 1, 2003

(54) VARIETY OF GERANIUM PLANT NAMED 'PACAMLA'

(75) Inventor: Andrea Michalik, Dresden (DE)

(73) Assignee: Deutsche Saatgutgesellschaft m.b.H., Berlin (DE)

( * ) Notice: Subject to any disclaimer, the term of this patent is extended or adjusted under 35 U.S.C. 154(b) by 0 days.

(21) Appl. No.: 10/007,139

(22) Filed: Dec. 4, 2001

(51) Int. Cl.[7] ..... A01H 5/00
(52) U.S. Cl. ..... Plt./325
(58) Field of Search ..... Plt./325, 329

(56) References Cited

PUBLICATIONS

GTITM UPOVROM Citation for 'Pacamla' as per QZ PBR 991808; Dec. 13, 1999.*

* cited by examiner

*Primary Examiner*—Kent Bell
(74) *Attorney, Agent, or Firm*—Webb Ziesenhiem Logsdon Orkin & Hanson, P.C.

(57) ABSTRACT

A new and distinct early flowering zonal geranium plant with red-purple colored petals with a lighter colored eye, compact and vigorous growth and strong peduncles.

1 Drawing Sheet

BOTANICAL CLASSIFICATION

*Pelargonium×hortorun.*

VARIETAL DENOMINATION

'Pacamla'.

BACKGROUND OF THE INVENTION

The present invention comprises a new and distinct cultivar of *Pelargonium×hortorum* known by the varietal name 'Pacamla'. The new variety was discovered in a selected breeding program in Dresden, Germany. The new variety is the result of a cross between two unnamed and unpatented selections from a collection of 12–15 unnamed proprietary breeding plants. The flower color and habit of the new variety are similar to its parents but with different color intensity and flower shape. The new variety was first asexually reproduced in January 1999 by cuttings in Dresden, Germany. The new variety has been trial and field tested in Dresden and has been found to retain its distinctive characteristics and remain true to type through successive propagations.

The cultivar, when propagated in January and potted in February in a greenhouse in Dresden, Germany is ready for outdoor planting in May.

DESCRIPTION OF THE DRAWINGS

The accompanying photographic drawing illustrates the new variety, with the color being as nearly true as is possible with color illustrations of this type.

DESCRIPTION OF THE PLANT

The following detailed description sets forth the characteristics of the new cultivar. The data which defines these characteristics were collected by asexual reproductions by cuttings carried out in Dresden, Germany of a 9 month old potted plant in a 12 cm container. The color readings were taken on a plant outdoors in the shade. Color references are primarily to The R.H.S. Colour Chart of The Royal Horticultural Society of London.

PLANT

Form: Upright.
Height: 25–28 cm from soil to top of foliage; 40 cm from soil to top of umbels.
Growth: Erect, well-branched.
Width: 23 cm.
Strength: Does not require artificial support.
Foliage: Zone present; arrangement is opposite.
Time to develop roots: 3.5 weeks.
Description of roots: Yellow Group 11D; adventive.
Leaves:
- *Size.*—Length: 4–5 cm. Width: 7–8 cm.
- *Shape.*—Overall: Kidney-shaped. Base: Open. Apex: Pointed.
- *Margin.*—Bi-crenate.
- *Texture.*—Hairy.
- *Color.*—Upper surface: Green Group 137B. Lower surface: Green Group 137C.
- *Ribs and veins.*—Venation: Net-like. Color: Green Group 138A.
- *Zone color.*—Yellow-Green Group 147A.

Petioles:
- *Color.*—Green Group 138A.
- *Length.*—6 cm.
- *Diameter.*—2 mm.

Stem:
- *Length.*—18–20 cm.
- *Color.*—Green Group 138A.
- *Internode length.*—3–4 cm.
- *Lateral branch length.*—18–20 cm.

THE BUD

Shape when closed, just prior to opening:
- *Overall.*—Rounded.
- *Individual bud.*—Shell-shaped.
- *Size of individual bud.*—Length: 1.5–1.7 cm. Width: 1.0–1.2 cm.
- *Size of cluster.*—8–10 cm in diameter.
- *Color.*—Red-Purple Group 66A.

INFLORESCENCE

Blooming habit: Umbels.
*Size.*—Width: 10–14 cm. Depth: 10–14 cm.
*Borne.*—Umbel; flowers on pedicel; pedicel on peduncle.
*Number of flowers per umbel.*—20–30.
*Quantity of inflorescences per plant.*—12–16.
Flowers:
*Form.*—Zygomorphic.
*Size.*—Diameter: 4–5 cm. Depth: 1.0–1.5 cm.
*Petals.*—Color: Upper surface: Red-Purple Group 66A. Lower surface: Red-Purple Group 66D. Eye: Red-Purple Group 62D. Shape: Overall: Round to oval. Apex: Round. Base: Pointed. Size: Length: 2.3 cm. Width: 2.0 cm. Margin: Smooth. Number per flower: 7–9.
*Texture.*—Smooth.
*Tonality from a distance.*—Neon bright reddish-purple.
Sepals:
*Color.*—Upper surface: Yellow-Green Group 144A. Lower surface: Yellow-Green Group 144B.
*Shape.*—Overall: Pointed; narrow. Apex: Pointed. Base: Wider and not pointed.
*Size.*—Length: 1.0–1.2 cm. Width: 0.4–0.5 cm.
Petaloids:
*Quantity.*—3–4.
*Shape.*—Irregular, pointed apex with wider base.
*Size.*—Width: 2–4 mm. Length: 3–7 mm.
*Color.*—Upper surface: Red-Purple Group 71D. Lower surface: Red-Purple Group 68A.
Pedicel:
*Length.*—2.0 cm.
*Color.*—Greyed-Orange Group 175B.
Peduncle:
*Length.*—10 cm.
*Color.*—Green Group 143C.
Disease/pest resistance: No susceptibility to diseases or pests has been noted to date.
Flowering season: Spring until frost.
Lastingness of an individual bloom on the plant: 4 weeks.

REPRODUCTIVE ORGANS

Stamens:
*Anthers.*—3 mm long.
*Filaments.*—Length: 0.5 cm. Color: Red-Purple Group 69D. Pollen: Abundant; colored Orange-Red Group 32A.
Pistils:
*Number.*—One; five parted.
*Length.*—0.3–0.4 cm.
*Stigma color.*—Red-Purple Group 66A.
*Style.*—Length: 0.8 cm. Color: Green Group 141D.
*Ovaries.*—Superior; hairy; 0.4 cm long; Green Group 140C.
Seeds: Rarely present.
*Amount.*—5 per flower maximum.
*Size.*—1 mm wide; 4 mm long.
*Color.*—Greyed-Orange Group 165A.

GENERAL CHARACTERISTICS

'Pacamla' has the following general characteristics.

1. Compact growth.
2. Vigorous growth habit.
3. Short development time and early flowering.
4. Stable and upright peduncles.
5. Petals with light colored eye.
6. Rounded umbel.
7. Well-shaped.
8. Long-lasting.
9. Attractive from a distance.

I claim:

1. A new and distinct variety of geranium plant substantially as shown and described.

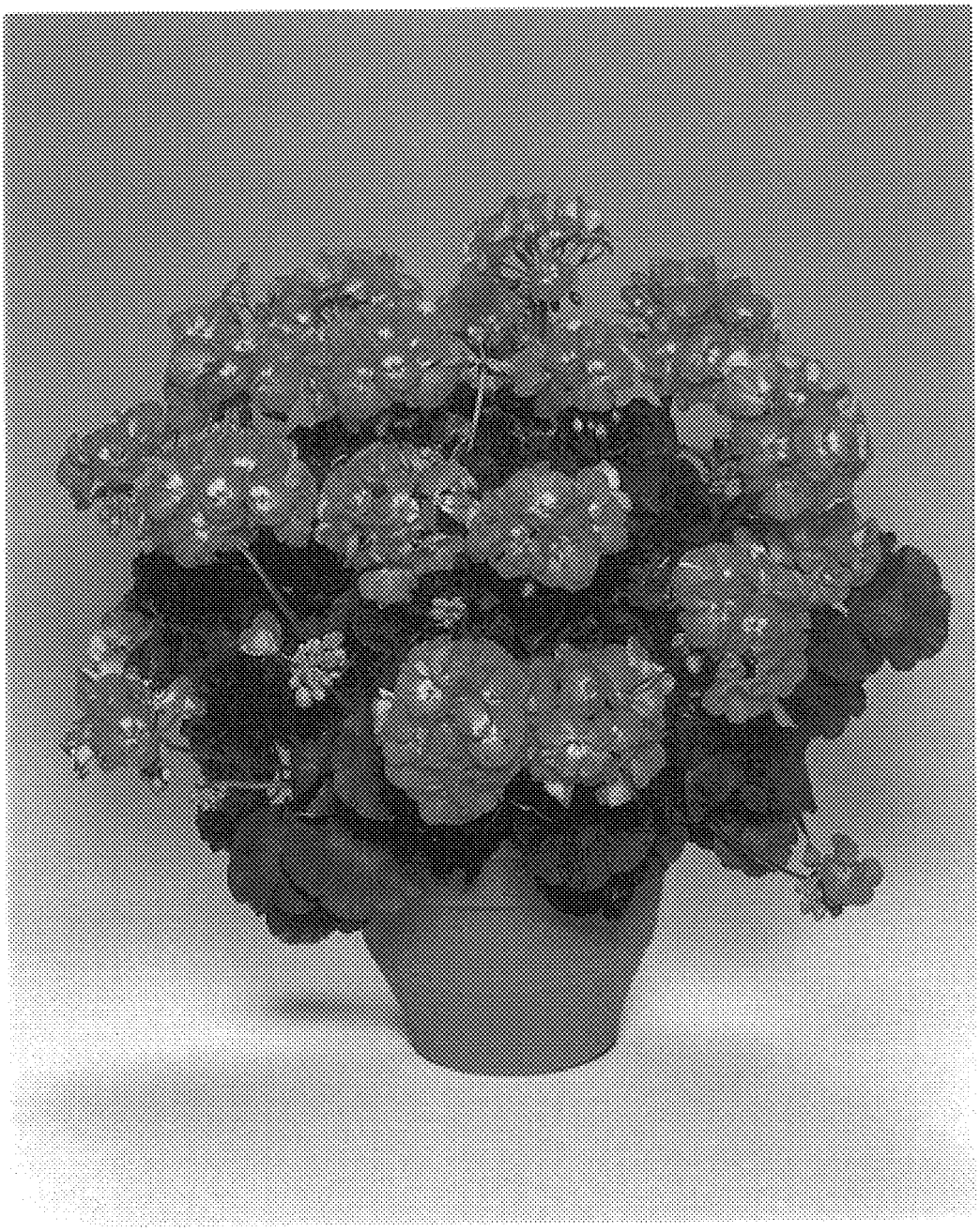

* * * * *